United States Patent

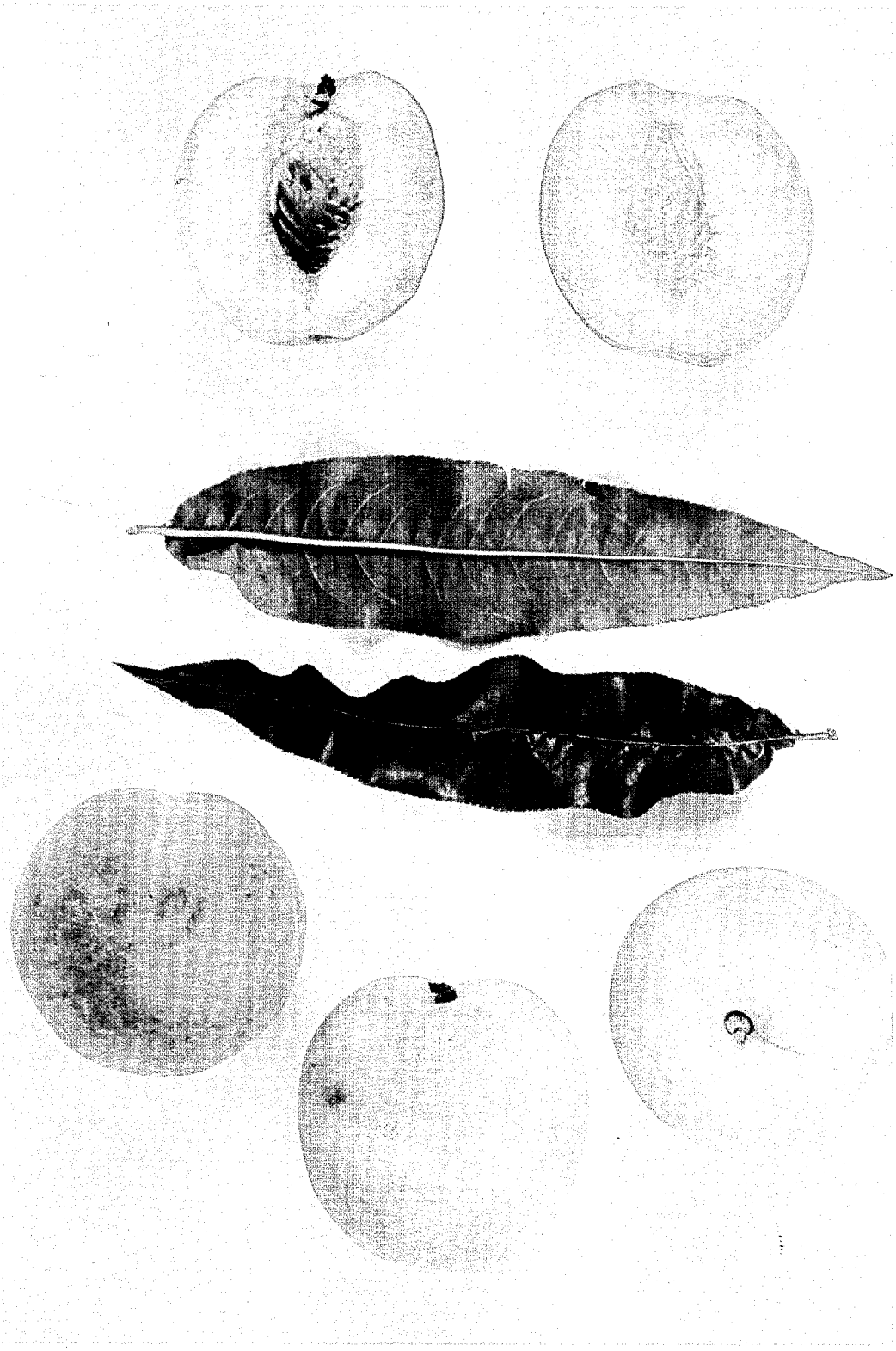

Plant Pat. 3,965
Patented Oct. 26, 1976

3,965
PEACH TREE

Alexander C. McLeod, Rte. 1, McBee, S.C. 29101

Filed Aug. 4, 1975, Ser. No. 601,799
Int. Cl.[2] A01H *5/03*
U.S. Cl. Plt.—43 1 Claim This invention relates to a new and distinct variety of peach tree which bears medium to large fairly uniform peaches.

The fruit of the new and distinct variety of peach tree is characterized especially by its most attractive appearance and excellent marketable quality for dessert use, which are especially desirable at the ripening season of this peach variety when other varieties are scarce. This new variety ripens 7–10 days before the Loring peach (unpatented). The fruit is very attractive, having bright red cheeks and having a bright golden ground color diffused with red. It is symmetrical in shape and smooth, having a smooth suture line and having less tendency to flatten than the Rio Oso Gem (U.S. Pat. No. 84). Its flavor is that of a sweet mild peach with firm but melting flesh texture. The flesh of the peach is yellow and its stone is of the semi-cling to free type. Another characteristic of the fruit is a tendency of non-browning of the flesh.

The new variety of peach tree was found by me as what is thought by me to be a chance budsport of Loring in my cultivated orchard two miles southeast of McBee, S.C. The budsport is a one limb mutation. This variety is a true sport. The budsport has been asexually reproduced by me by being top worked by budding on Norman trees (unpatented) at my cultivated Norman orchard near McBee, S.C. Such asexual reproduction at maturity and when in bearing, having been found to run true to the parent tree in all respects.

The accompanying drawing, in the form of a photograph, shows typical specimens of the leaves and fruit of my new variety of peach tree with the upper and lower surfaces of the leaves being illustrated, and with top, bottom, and side exterior views and sectonal views of the fruit being shown all depicted in color as nearly true as it is reasonably possible to make the same in color illustration of this character.

The following is a detailed description of the characteristics of my new variety as based upon observations of specimens grown at my orchard referred to above, with color terminology in accordance with Munsell's Book of Color, Munsell Color Company, Baltimore, Md., 1929–1960, except where general color terms of ordinary dictionary significance are obvious.

Tree:
- Size—Medium
- Vigor—Average
- Growth—Slightly more spreading than upright
- Density—Medium
- Form—Globular to conical
- Hardiness—Average
- Production—Average to Heavy
- Bearing—Good and regular Trunk:
- Size—Medium
- Texture—Medium Branches:
- Size—Medium
- Texture—Medium
- Color—Brownish to gray
- Lenticels—Scarce to medium number, small to medium in size Leaves:
- Size—Medium average length 7¾ inches. Average width 1⅞ inches
- Form—Lanceolate, acuately pointed
- Thickness—Medium
- Texture—Smooth to slightly crinkled, along the midrib
- Margin—Serrate
- Petiole—Average length 7½ inches, medium thickness
- Glands—Reniform occurring mostly on base of petiole, sometimes one opposite, sometimes two opposite and occasionally one gland on the leaf blade
- Stipules—Inconspicuous
- Color (mature leaves)—Top side—hue 2.4GY 5/6, under side—5GY 6/8

Flower buds:
- Hardness—Medium
- Size—Medium large
- Length—Medium
- Form—Plump
- Pubescence—Medium Flowers:
- Blooming period—Early, indicating short chilling requirements
- Size—Large showy
- Color—Pink Fruit:
- Maturity when described—Eating ripe
- First picking—June 18, 1975
- Last picking—June 25, 1975
- Size—Medium to large fairly uinform. Average trasversely in suture plane 2⅝ to 2⅞ inches. Average diameter axially 2⅝ inches
- Form—Uniform, symmetrical globose to slightly elongated
- Suture—Distinct, shallow and extends slightly beyond the apex showing slight depression beyond pistil point
- Ventral surface—Rounded
- Cavity—Short, narrow and deep
- Base—Oblique to rounded
- Apex—Short
- Pistil point—Depressed to slightly raised Skin:
- Thickness—Medium
- Texture—Medium
- Tendency to crack—None
- Down—Light and short
- Color—Check hue 5R 3/6. Ground hue 2YR 6/10

Flesh:
- Juice—Medium
- Texture—Firm but melting
- Fibers—Slightly fibrous but tender
- Ripens—Evenly
- Flavor—Subacid with slight indication of soluble tannin tending to lend full bodied flavor
- Aroma—Normal peach aroma
- Eating quality—Excellent
- Color—Hue 10YR 8/8
- Surface of pit cavity—Red with yellowish red fibers Stone:
- Type—Semi-cling to free
- Size—Medium. Average length 1½ inches to 1¾ inches. Average breadth 1 inch to 1⅛ inches. Average thickness ¾ inches to 1 inch
- Form—Elliptical rhomboid with slight central bulge
- Base—Straight
- Sides—Equal Surface—European—Elberta
Ridges—Usually rounded toward base on either side but sometimes slight jagged
Pits—Elongated
Tendency to split—None
Color—7.5R 6/8

Use: Market, dessert
Keeping quality: Excellent
Shipping quality: Excellent

The tree and its fruit herein described may vary in slight detail due to climatic and soil conditions under which the variety may be grown.

What is claimed:

1. A new and distinct variety of peach tree substantially as shown and described characterized particularly as to novelty by fruit having the combination of an early ripening season 7–10 days before the Loring peach, a most attractive form being slightly elongated from apex to cavity, having a bright red cheek and bright golden ground color diffused with red, a smooth suture line and having less tendency to flatten than the Rio Oso Gem peach, a most delicious flavor sub-acid with slight indication of soluble tannin tending to lend full bodied flavor, and tendency to non-browning of the flesh.

No references cited.

ROBERT E. BAGWILL, Primary Examiner